United States Patent [19]

Hashiba et al.

[11] Patent Number: 5,847,199

[45] Date of Patent: Dec. 8, 1998

[54] DERIVATIVE OF PHOSPHONIC ACID AND PROCESS FOR THE PREPARATION THEREOF

[75] Inventors: Isao Hashiba; Kenichi Tokunaga, both of Funabashi, Japan

[73] Assignee: Nissan Chemical Industries, Ltd., Tokyo, Japan

[21] Appl. No.: 957,026

[22] Filed: Oct. 24, 1997

[30] Foreign Application Priority Data

Nov. 14, 1996 [JP] Japan ..................................... 8-302716

[51] Int. Cl.$^6$ .................................. C07F 9/38; C07F 9/40
[52] U.S. Cl. ................................. 562/8; 558/180
[58] Field of Search ................................. 562/8; 558/180

[56] References Cited

U.S. PATENT DOCUMENTS 2,834,804 5/1958 Lecher et al. ........................... 260/515

5,498,784 3/1996 Arnold et al. ........................... 528/337

FOREIGN PATENT DOCUMENTS 44-24688-B 10/1969 Japan .

*Primary Examiner*—Alan L. Rotman
*Assistant Examiner*—Charanjit S. Aulakh
*Attorney, Agent, or Firm*—Oliff & Berridge, PLC

[57] ABSTRACT

To provide 2,5-dicarboxyphenyl phosphonic acid and a process for the preparation thereof, comprising the steps of: forming a reaction liquid phase by supplying a 2,5-dialkylphenyl phosphonic acid, a solvent, a cobalt salt, a manganese salt and/or a cerium salt, and bromine or a bromine compound into a reaction zone; and supplying oxygen into the reaction liquid phase by bringing an oxygen-containing gas into contact with the reaction liquid phase by supplying an oxygen-containing gas into the above-mentioned reaction zone.

5 Claims, No Drawings

DERIVATIVE OF PHOSPHONIC ACID AND PROCESS FOR THE PREPARATION THEREOF

BACKGROUND OF THE INVENTION

1. Field of the invention

The present invention relates to 2,5-dicarboxyphenyl phosphonic acid which is a novel compound and a process for the preparation thereof.

2. Description of the Related Art

Japanese Examined Patent Publication No. Sho 44-24688 (1969) (hereinafter referred to as JP-B-44-24688(1969)) discloses a modified polyethylene terephthalate containing 3,5-dicarboxyphenyl phosphonic acid as a copolymerized component.

JP-B-44-24688(1969) does not disclose 2,5-dicarboxyphenyl phosphonic acid and a process for the preparation of 3,5-dicarboxyphenyl phosphonic acid.

SUMMARY OF THE INVENTION

An object of the present invention is to provide 2,5-dicarboxyphenyl phosphonic acid and a process for the preparation of thereof.

According to the present invention, 2,5-dicarboxyphenyl phosphonic acid can be prepared by a process which comprises the steps of: forming a reaction liquid phase by supplying 2,5-dialkylphenyl phosphonic acid, a solvent, a cobalt salt, a manganese salt and/or a cerium salt, and bromine or a bromine compound into a reaction zone; and supplying oxygen into the reaction liquid phase by bringing an oxygen-containing gas into contact with the reaction liquid phase by supplying an oxygen-containing gas into the above-mentioned reaction zone.

DETAILED DESCRIPTION OF THE PREFERRED EMBODIMENT

Two alkyl groups contained in 2,5-dialkylphenyl phosphonic acid which is a raw material are not particularly limited, each may be the same or different with each other, and may have branched chains. Examples of the preferred alkyl groups include methyl, ethyl, n-propyl, isopropyl, n-butyl, isobutyl, n-pentyl, and the like, and as examples of the preferred 2,5-dialkylphenyl phosphonic acid, there are exemplified 2,5-dimethylphenyl phosphonic acid, 2-methyl-5-ethylphenyl phosphonic acid, 2-ethyl-5-propylphenyl phosphonic acid, 2-methyl-5-methylphenyl phosphonic acid, 2-propyl-5-methylphenyl phosphonic acid, 2,5-diethylphenyl phosphonic acid, 2,5-dipropylphenyl phosphonic acid, and the like. Above all, 2,5-dimethylphenyl phosphonic acid is more preferred from a commercial viewpoint.

2,5-dialkylphenyl phosphonic acid can be prepared by, for example: heating a mixture composed of a 2,5-dialkylbenzene phosphonothioic dichloride and water under refluxing; or causing hydrolysis of the 2,5-dialkylbenzene phosphonothioic dichloride by heating a mixture at 30° to 80° C. in which a dilute nitric acid is added to a benzene solution of the 2,5-dialkylbenzene phosphonothioic dichloride. Also, the 2,5-dialkylbenzene phosphonothioic dichloride can be prepared, for example, by a method in which a 1,4-dialkylbenzene and thiophosphoryl trichloride are heated at a temperature of 50° to 200° C. or so, in the presence of aluminum chloride as a catalyst.

As other examples of a process for the preparation of the 2,5-dialkylphenyl phosphonic acid, there is exemplified a process in which a 2,5-dialkylbenzene bromide is reacted with trimethyl phosphite in the presence of nickel as a catalyst to prepare a dimethylester of the 2,5-dialkylphenyl phosphonic acid, and then a mixture composed of the dimethylester of the 2,5-dialkylphenyl phosphonic acid and hydrochloric acid is heated under refluxing to thereby cause hydrolysis of the dimethylester of the 2,5-dialkylphenyl phosphonic acid.

As the metallic salts, a mixture composed of a cobalt salt, a manganese salt and/or a cerium salt is employed, such as: a mixture composed of a cobalt salt, a manganese salt, and a cerium salt; a mixture composed of a cobalt salt and a manganese salt; and a mixture composed of a cobalt salt and a cerium salt. The metallic salts are used in a proportion of 0.01 to 20% by mol, preferably 2 to 10% by mol based on the 2,5-dialkylphenyl phosphonic acid.

Examples of the cobalt salt include: a cobalt salt of fatty acid such as cobalt formate, cobalt acetate, cobalt octylate, or cobalt naphtate; a chelate compound of cobalt such as cobalt acetylacetonate; and a cobalt salt of an inorganic acid such as cobalt chloride, cobalt bromide, cobalt iodide, or cobalt carbonate. Examples of the manganese salt include: a manganese salt of a fatty acid such as manganese formate, manganese acetate, manganese octylate, or manganese naphtate; a chelate compound of manganese such as manganese acetylacetonate; and a manganese salt of an inorganic acid such as manganese chloride, manganese bromide, manganese iodide, or manganese carbonate, etc. Examples of the cerium salt include: a cerium salt of a fatty acid such as cerium formate, cerium acetate, cerium octylate, or cerium naphtate; a chelate compound of cerium such as cerium acetylacetonate; and a cerium salt of an inorganic acid such as cerium chloride, cerium bromide, cerium iodide, or cerium carbonate, etc. The cobalt salts, the manganese salts, and the cerium salts may be employed solely or in combination of two or more kinds, respectively.

The bromine compound is not particularly limited, and a variety of bromine compounds may be employed. As preferred examples, there are exemplified hydrogen bromide and a salt thereof such as, for example, antimony bromide, sodium bromide, and potassium bromide. Bromine or the bromine compounds may be employed solely or in combination of two or more kinds. Those are employed in a proportion of 0.1 to 20% by mol, and preferably 1–20% by mol based on the 2,5-dialkylphenyl phosphonic acid. The proportion in % by mol of bromine or bromine compounds to be employed based on the 2,5-dialkylphenyl phosphonic acid is preferably larger than that of the above-mentioned metallic salts to be employed based on the 2,5-dialkylphenyl phosphonic acid.

As the solvents, an alkanoic acid having a carbon number of 1 to 3 is preferred, and the examples thereof include formic acid, acetic acid, and propionic acid, etc. Acetic acid is more preferred from a commercial viewpoint. The solvents are employed in an amount of 1 to 100 times by weight, and preferably 5 to 20 times by weight based on the 2,5-dialkylphenyl phosphonic acid. Although the oxygen-containing gas may be a gas which is oxygen gas alone, a mixed gas composed of oxygen gas and other inert gases, for example, a gas mixed with nitrogen gas, air, and the like are preferred.

The reaction liquid phase is formed by supplying the cobalt salt, the manganese salt and/or the cerium salt, bromine or the bromine compound, the solvent, and the 2,5-dialkylphenyl phosphonic acid in the above-mentioned proportion, into the reaction zone, for example, a reaction vessel. Into the reaction zone, the oxygen-containing gas is supplied, and the gas supplies oxygen to the reaction liquid phase by bringing into contact with the above-mentioned reaction liquid phase. The 2,5-dialkylphenyl phosphonic acid in the reaction liquid phase is oxidized by oxygen supplied from the oxygen-containing gas, resulting in forming 2,5-dicarboxyphenyl phosphonic acid. The above-mentioned metallic salts and bromine or the bromine compound supplied into the reaction liquid phase contribute to formation of a catalyst that accelerates the oxidation reaction in the reaction liquid phase. The oxidation reaction in the reaction liquid phase can be conducted, preferably under agitating, in a temperature of 100° to 350° C., preferably 120° to 300° C., and under pressurization of the oxygen-containing gas of from an ordinary pressure to 400 atm, and preferably from 10 to 100 atm, particularly, under pressurization by partial pressure of oxygen of from an ordinary pressure to 80 atm, and more preferably from 2 to 50 atm. Formation of the reaction liquid phase and supply of the oxygen-containing gas can be conducted by any one of a continuous or batchwise method. The oxidation reaction can be usually terminated in 1 to 20 hours or so.

EXAMPLE

Example 1

A glass-made reaction vessel was charged with 42.6 g of p-xylene, 180 g of thiophosphoryl trichloride, and 40 g of aluminum chloride, followed by heating a mixture in the reaction vessel at 80° C. for 3 hours while agitating. After the completion of heating, the mixture in the reaction vessel was cooled to a room temperature, and then, water and n-heptane were added into the reaction vessel, followed by settling to separate into water phase and an n-heptane phase after agitating. The n-heptane phase was further washed by water, and distilled at 140° C. and reduced pressure of 0.3 mmHg to collect 30 g of a distillate which is 2,5-dimethylbenzene phosphonothioic dichloride.

A glass-made reaction vessel was charged with 30 g of 2,5-dimethylbenzene phosphonothioic dichloride collected as described above, 100 g of benzene, and 50 g of water, followed by heating while agitating until temperature of a liquid in the reaction vessel attains to 50° C. Subsequently, a small amount of nitric acid having 63% by weight was added dropwise into the liquid in the reaction vessel which is agitated, and there were observed heat generation of the liquid in the reaction vessel and generation of a nitrogen oxide gas, and further, the above-mentioned nitric acid was continued to gradually add dropwise, followed by terminating to add dropwise 40 g of the above-mentioned nitric acid which is total amount. After the completion of dropwise addition of the nitric acid, it was further continued to agitate for 3 hours, and then the liquid in the reaction vessel was cooled to 10° C. A crystal was deposited by cooling. Contents in the reaction vessel were flown through a filter, and the crystal on the filter was washed by adding water, followed by drying to obtain 16.5 g of 2,5-dimethylphenyl phosphonic acid which is a solid. It was calculated that yield is 67.7% based on 2,5-dimethylbenzene phosphonothioic dichloride.

A titanium-made autoclave having internal capacity of 100 ml was charged with 5.58 g of 2,5-dimethylphenyl phosphonic acid obtained as mentioned above, 0.3 g of cobalt acetate salt having $4H_2O$, 0.074 g of manganese acetate salt having $4H_2O$, 0.41 g of an aqueous solution containing 47% by weight of hydrogen bromide, and 55 g of acetic acid. Into the autoclave, nitrogen gas was supplied until internal pressure attains to 70 atm, followed by supplying oxygen gas until internal pressure attains to 100 atm. Liquid was heated to temperature of 220° C. by heating the autoclave while agitating a liquid in the autoclave, and then pressure in the autoclave was maintained at 100 atm for 8 hours by continuing to supply oxygen gas as described above. Heating was immediately stopped, and the autoclave was cooled to ordinary temperature.

After reducing pressure in the autoclave, contents were taken out from the autoclave and filtered, and a solid deposited on a filter material was washed by pouring acetic acid, followed by drying the deposited solid to obtain 4.5 g of the deposited solid.

The deposited solid was purified by developing with a mixed liquid composed of methanol of 70% by weight and acetic acid of 30% by weight using a silica gel column to obtain 3.4 g of a white-colored crystal showing a melting point of 288° to 290° C. Yield was calculated to be 47.4% based on dimethylphenyl phosphonic acid which is a raw material.

The white-colored crystal showed an absorption by carbonyl group at 1,690 $cm^{-1}$ in an infrared absorption analysis, and a peak by carbon atom in two kinds of carbonyl group in a nuclear magnetic resonance analysis, respective contents of 39.1% by weight of carbon, 2.9% by weight of hydrogen, and 12.5% by weight of phosphorus in an elementary analysis, and although it did not show a parent peak in a mass spectroscopy, it showed a peak in molecular weight of 229. The above mentioned results in the elementary analysis well coincide with respective contents of 39.0% by weight of carbon, 2.9% by weight of hydrogen, and 12.6% by weight of phosphorus which are calculated from the chemical formula of 2,5-dicarboxyphenyl phosphonic acid.

Separately, a methylated compound obtained from the above-mentioned white-colored crystal with a methylation method by diazo methane showed a peak by methyl group at four positions in a nuclear magnetic resonance analysis, and showed the presence of a substance having a molecular weight of 302 in a mass spectroscopy. Accordingly, a molecular weight was calculated to be 246 in a substance before methylation of the substance having the molecular weight of 302, and it is identified that it coincided with the molecular weight of 2,5-dicarboxyphenyl phosphonic acid. From the results in the above analyses, it is identified that the above-mentioned white-colored crystalline compound is 2,5-dicarboxyphenyl phosphonic acid represented by the formula described below,

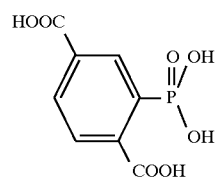

[Chemical formula 1]

, and the above-mentioned methylated compound having the molecular weight of 302 is tetramethyl ester of 2,5-dicarboxyphenyl phosphonic acid represented by the formula described below.

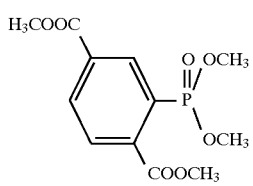

[Chemical formula 2]

Example 2

The same autoclave employed in Example 1 was charged with 5.58 g of 2,5-dimethylphenyl phosphoric acid obtained by the same method as in Example 1, 0.3 g of cobalt acetate salt having $4H_2O$, 0.05 g of cerium acetate salt having $1H_2O$, 0.41 g of an aqueous solution containing 47% by weight of hydrogen bromide, and 55 g of acetic acid. Into the autoclave, nitrogen gas was supplied until internal pressure attains to 70 atm, followed by supplying oxygen gas until internal pressure attains to 100 atm. Liquid was heated to the temperature of 250° C. by heating the autoclave while agitating a liquid in the autoclave, and then pressure in the autoclave was maintained at 100 atm for 10 hours by continuing to supply oxygen gas as described above. Heating was immediately stopped, and the autoclave was cooled to ordinary temperature.

After reducing pressure in the autoclave, the contents were taken out from the autoclave and filtered, and a solid deposited on a filter material was washed by pouring acetic acid, followed by drying the deposited solid to obtain 5.0 g of the deposited solid.

Example 3

The same autoclave employed in Example 1 was charged with 5.58 g of 2,5-dimethylphenyl phosphonic acid obtained by the same method as in Example 1, 0.3 g of cobalt acetate salt having $4H_2O$, 0.07 g of manganese acetate salt having $4H_2O$, 0.5 g of liquefied bromine, and 55 g of acetic acid. Into the autoclave, nitrogen gas was supplied until internal pressure attains to 70 atm, followed by supplying oxygen gas until internal pressure attains to 100 atm. Liquid was heated to the temperature of 250° C. by heating the autoclave while agitating a liquid in the, autoclave, and then pressure in the autoclave was maintained at 100 atm for 10 hours by continuing to supply oxygen gas as described above. Heating was immediately stopped, and the autoclave was cooled to ordinary temperature.

After reducing pressure in the autoclave, the contents were taken out from the autoclave and filtered, and a solid deposited on a filter material was washed by pouring acetic acid, followed by drying the deposited solid to obtain 5.0 g of the deposited solid.

Example 4

A glass-made reaction vessel was charged with 203.4 g (0.08 mol) of bis(hydroxyethyl)terephthalate, 66.45 g (0.40 mol) of terephthalic acid, and 37.22 g (0.60 mol) of ethylene glycol, followed by heating a mixture in the reaction vessel at 260° C. for 3 hours while agitating in an atmosphere of nitrogen and under ordinary pressure to obtain a reaction product in esterification.

And, the reaction vessel was charged with the reaction product in esterification, 18.25 g (74 millimole, 1.0% by weight as phosphorus atom based on a polyester resin produced) of 2,5-dicarboxyphenyl phosphonic acid, 0.14 g (0.5 millimole) of antimony trioxide, 0.015 g (0.06 millimole) of cobalt acetate salt having $4H_2O$, followed by heating at 270° C. for 3 hours while agitating under ordinary pressure. Subsequently, the pressure was gradually reduced until the final pressure attains to 40 mmHg while agitating, and a condensation polymerization was conducted while heating at 280° C. for 1 hour to obtain a polyester resin product. Intrinsic viscosity "η" was measured by a mixture composed of the same weight of phenol and 1,1,2,2-tetrachloroethane at the temperature of 25° C. The intrinsic viscosity "η" was 0.72. Further, flame retardancy in the resin thus obtained was evaluated by measuring a flame retardancy index (Oxygen Index: OI) of test pieces which were molded from the resin according to the flame retardancy testing method (JIS D1201). Oxygen Index showing a self-flash hindering property requires not less than 22–23, and in the case that a higher flame retardancy is required, there is required not less than 27–28. Oxygen Index in the resin obtained was 30.3, and it shows a high flame retardancy.

2,5-dicarboxyphenyl phosphonic acid can be readily obtained by oxidation with oxygen of a 2,5-dialkylphenyl phosphonic acid as a raw material under the presence of a catalyst, and it can be employed in a variety of uses.

2,5-dicarboxyphenyl phosphonic acid has two carboxylic groups which can form an ester. Accordingly, a polyester can be formed by a condensation polymerization of 2,5-dicarboxyphenyl phosphonic acid with a polyvalent alcohol such as ethylene glycol. Also, the polyester shows a reactivity by hydroxyl group in phosphonic acid contained in a proportion of 2 pieces per two ester groups, and, for example, it produces a colored polyester by connecting to a molecule of a reactive dye. Phosphorus atoms contained in the polyester give also flame retardancy to the polyester. The polyester can be also employed as an additive for other polymers. 2,5-dicarboxyphenyl phosphonic acid can form an epoxy resin by a reaction with an epoxy compound, and a polyamide by a reaction with a polyisocyanate. As described above, 2,5-dicarboxyphenyl phosphonic acid is not only employed as a monomer for preparing a polymer, but also 2,5-dicarboxyphenyl phosphonic acid itself can be employed as additives such as an agent for giving transparency and a flame retardant for a variety of polymers or resins.

What is claimed is:

1. 2,5-dicarboxyphenyl phosphonic acid.

2. A process for the preparation of 2,5-dicarboxyphenyl phosphonic acid, comprising the steps of:

forming a reaction liquid phase by supplying 2,5-dialkylphenyl phosphonic acid, a solvent, a cobalt salt, a manganese salt and/or a cerium salt, and bromine or a bromine compound into a reaction zone; and supplying oxygen into the reaction liquid phase by bringing an oxygen-containing gas into contact with the reaction liquid phase by supplying an oxygen-containing gas into the above-mentioned reaction zone.

3. A process for the preparation of 2,5-dicarboxyphenyl phosphonic acid as claimed in claim 2, wherein said 2,5-dialkylphenyl phosphonic acid is 2,5-dimethylphenyl phosphonic acid.

4. A process for the preparation of 2,5-dicarboxyphenyl phosphonic acid as claimed in claim 2, wherein said solvent is acetic acid.

5. A process for the preparation of 2,5-dicarboxyphenyl phosphonic acid, comprising the steps of:

forming a reaction liquid phase by supplying 2,5-dimethylphenyl phosphonic acid, acetic acid, a cobalt salt, a manganese salt and/or a cerium salt, and bromine or a bromine compound into a reaction zone; and supplying oxygen into the reaction liquid phase by bringing an oxygen-containing gas into contact with the reaction liquid phase by supplying an oxygen-containing gas into the above-mentioned reaction zone.

* * * * *